United States Patent [19]

MacLeod

[11] Patent Number: 4,821,326

[45] Date of Patent: Apr. 11, 1989

[54] NON-AUDIBLE SPEECH GENERATION METHOD AND APPARATUS

[75] Inventor: Norman MacLeod, Sunnyvale, Calif.

[73] Assignee: Macrowave Technology Corporation, San Jose, Calif.

[21] Appl. No.: 121,659

[22] Filed: Nov. 16, 1987

[51] Int. Cl.$^4$ ............................................. G10L 7/02
[52] U.S. Cl. ...................................... 381/51; 381/70; 364/513.5; 623/9
[58] Field of Search .................................. 381/36–40, 381/51, 70, 86; 364/513.5; 623/9

[56] References Cited

U.S. PATENT DOCUMENTS

| | | | |
|---|---|---|---|
| 3,914,550 | 10/1975 | Cardwell, Jr. | 381/70 |
| 4,292,472 | 9/1981 | Lennox | 381/70 |
| 4,338,488 | 7/1982 | Lennox | 381/70 |
| 4,473,905 | 9/1984 | Katz et al. | 381/70 |
| 4,502,150 | 2/1985 | Katz et al. | 381/70 |
| 4,550,427 | 10/1985 | Katz et al. | 381/70 |
| 4,571,739 | 2/1986 | Resnick | 381/70 |
| 4,612,664 | 9/1986 | Walsh et al. | 381/70 |
| 4,627,095 | 12/1986 | Thompson | 381/70 |
| 4,633,864 | 1/1987 | Walsh | 623/9 X |
| 4,672,673 | 6/1987 | Katz et al. | 381/70 |

Primary Examiner—Peter S. Wong
Assistant Examiner—Emanuel T. Voeltz
Attorney, Agent, or Firm—Rosenblum, Parish & Bacigalupi

[57] ABSTRACT

A non-audible speech generation apparatus and method for producing non-audible speech signals which includes an ultrasonic transducer or vibrator for projecting a series of glottal shaped ultrasonic pulses to the vocal track of a speaker. The glottal pulses, in the approximate frequency spectrum extending from fifteen kilohertz to one hundred five kilohertz, contain harmonics of approximately 30 times the frequency of the acoustical harmonics generated by the vocal cords, but which may nevertheless be amplitude modulated to produce non-audible speech by the speaker's silently mouthing of words. The ultrasonic speech is then received by an ultrasonic detector disposed outside of the speaker's mouth and electrically communicated to a translation device which down converts the ultrasonic signals to corresponding signals in the audible frequency range and synthesizes the signals into artificial speech.

26 Claims, 4 Drawing Sheets

NON-AUDIBLE SPEECH GENERATION METHOD AND APPARATUS

BACKGROUND OF THE INVENTION

1. Field of the Invention

The present invention relates generally to artificial speech aids, and more particularly, to a method and apparatus for generating non-audible artificial speech.

2. Discussion of the Prior Art

A number of devices have been developed which either replace the larynx (including the vocal cords) or otherwise artificially create comprehensible speech. The production of speech begins in the lungs which supply the air that is required to vibrate the vocal cords and carry the tune that is produced through the throat or pharynx and out of the nose and mouth. When a person desires to produce speech, the muscles controlling the vocal cords are tightened, thereby allowing the air passing through the larynx to cause the vocal cords to vibrate, which in turn produces a tone. The amplitude of the tone produced by the vocal cords is proportional to the amount of air supplied by the lungs. Modulation of the tone into comprehensible speech is caused by variations in the movement and positioning of the tongue, nasal cavity, throat and mouth.

Prior art artificial speech generation devices have been primarily designed to replace the larynx or vocal cords of persons whom have suffered either a permanent or temporary injury to that portion of their vocal track. Due to the injury suffered, the person is incapable of producing a tone for modulation. To solve this problem, U.S. Pat. No. 4,571,739, issued Feb. 18, 1986, to Resnick, discloses using an artificial tooth inserted into the mouth, constructed out of tone emitting components, for producing a tone which may then be modulated by the mouth, pharynx and nasal cavity of a laryngectomy patient. Similarly, U.S. Pat. No. 4,550,427, issued Oct. 29, 1985, to Katz et al, disclose a completely self-contained intraoral artificial larynx, having its own power source, tongue activated control, power saving signal generation circuitry, acoustic and audio amplifiers, and intraoral speaker, all of which are contained within an otherwise conventional dental prosthesis. Like the Resnick device, the device in Katz et al is designed for usage by laryngectomy patients, and in addition to tone production, provides some tone amplification and enhancement. Both prior art devices are designed to be operated only when the larynx is inoperative or missing.

Additional prior art devices also supply a certain quantity of air, in addition to the tone, into the oral cavity. In U.S. Pat. No. 4,612,664, issued Sept. 16, 1986, to Walsh et al, a solenoid reed valve capable of producing an amplitude modulated tone is disclosed. The reed valve replaces the amplitude modulation function of the lungs by regulating the quantity of air passing through a pressurized air passage created in the valve, which in turn creates a tone of sufficient amplification. U.S. Pat. No. 4,627,095, issued Dec. 2, 1986, to Thompson, discloses an artificial voice apparatus having a pump for producing an air flow within a tube connected to a sounding mechanism, thereby combining an audible tone with air flow. The tube is then coupled to a mouth piece and tone is transported into the person's mouth where the tongue, lips and teeth articulate the sound into speech. In these prior art devices, it is assumed that an audible tone is required to replace the vocal cords of the person using the device. However, if a person simply desires to speak without using their vocal cords, the transmission of an audible tone into the person's mouth would make it impossible to create artificial speech while at the same time restricting the audible emission of that speech from the mouth.

A large number of applications exist for nonaudible speech communication, such as in surveillance operations, military operations, or even where a person simply wishes to not be overheard while speaking in a private telephone conversation. Likewise, there are a number of situations in which surrounding or background noise is so great, that common levels of conversation or even high amplitude speech cannot be heard, such as at airports, on the battlefield, or in industrial environments. Finally, there are a number of applications, where audible speech itself, although desired, may be too awkward or distracting, such as in the case of dictation where the dictator is apparently only talking to himself. In such an instance, silently communicating to the dictation unit, which can record and playback an audible recording, may be an easier and more convenient means of communication than audible speech, and just as effective. However, inaudible artificial speech applications have previously been made unachievable with prior art artificial speech generation devices.

SUMMARY OF THE PRESENT INVENTION

It is therefore an object of the present invention to provide a non-audible artificial speech generation device.

Another object of the present invention is to provide a non-audible artificial speech generation device which allows a speaker to produce the artificial speech by simply talking, but without use of the vocal cords or use of unvoiced speech (whispering).

Another object of the present invention is to provide a non-audible artificial speech generation device which projects ultrasonic pulses to the vocal tract of a speaker from a ultrasonic transducer or by direct contact with the throat of the speaker.

A further object of the present invention is to provide a non-audible artificial speech generation device which projects ultrasonic pulses shaped like the glottal pulses which are produced by the larynx during the natural production of speech.

A still further object of the present invention is to provide a non-audible artificial speech generation device which uses a vocoder operating at ultrasonic frequency levels to translate and synthesize the non-audible artificial speech produced by a speaker into the audible range.

A still further object of the present invention is to provide a method for producing an artificial speech communication signal which can be used to operate a variety of devices.

Briefly, a preferred embodiment of the present invention comprises an ultrasonic transducer or vibrator for projecting a series of glottal shaped ultrasonic pulses to the vocal track of a speaker. The glottal pulses, in the approximate frequency spectrum extending from fifteen kilohertz to one hundred five kilohertz, contain harmonics of approximately 30 times the frequency of the acoustical harmonics generated by the vocal cords, but which may nevertheless be amplitude modulated to produce non-audible speech by the speaker's silently mouthing of words. The ultrasonic speech is then received by an ultrasonic detector disposed outside of the speaker's mouth and electrically communicated to a translation device which down converts the ultrasonic signals to corresponding signals in the audible frequency range and synthesizes the signals into artificial speech.

These and other objects of the present invention will no doubt become apparent to those skilled in the art after having read the following detail disclosure of the preferred embodiment which is illustrated in the several figures of the drawing.

IN THE DRAWING

DETAILED DESCRIPTION OF THE PREFERRED EMBODIMENT

Figure 1:
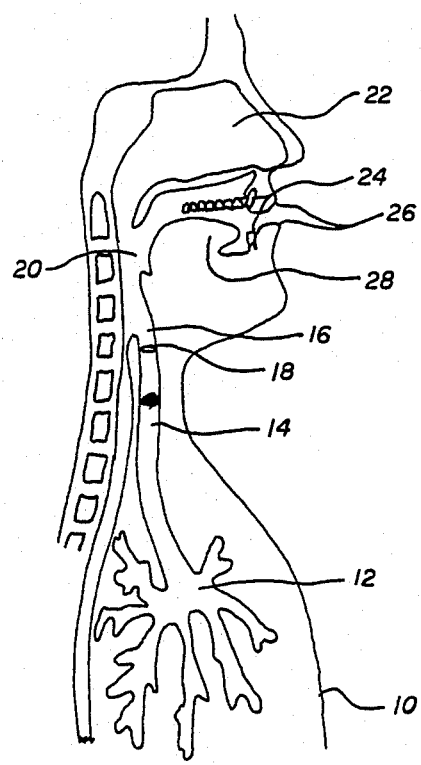
FIG. 1 is an anatomical diagram of human speech generating organs (the oral cavity).

Referring now to FIG. 1, an anatomical diagram of the speech generating organs of the human body 10 is shown, which may be utilized to properly illustrate the human production of speech. These organs and the area which they encompass, such as the lips and everything behind the lips, is referred to herein as the oral cavity. Air flows from the lungs 12, through the wind pipe (trachea) 14 and to the larynx 16. By voluntarily tightening the vocal cords 18, air passing across the vocal cords can be made to vibrate the vocal cords and cause them to emit a tone, much like the production of sound by a guitar string, except that air vibrates the cord or string rather than a finger or pick. The tone is then carried from the larynx to the throat 20 and the nasal cavity 22 and mouth for modulation.

The modulation function of the oral cavity may be demonstrated by fixing the mouth in an open position while causing the vocal cords to emit a constant tone. It will be noticed that the only change that can be created in the vocal output (without moving any parts of the mouth) is either a change in the pitch of the tone, or the amplitude of that tone. Thus, it can be seen, that speech is dependent upon two mutually exclusive groups of organs: (1) the lungs 12, trachea 14, and larynx 16, which create a tone and control the amplitude of that tone; and (2) the mouth and pharynx, which combine to modulate that tone into words. Practically any modification of any part of either group results in either no sound being produced, or the quality of the sound that is produced to suffer. In addition to the modulation of audible tones, the teeth 24, lips 26, and tongue 28 are also responsible to the production of non-vocal hissing noises that are required for the production of such sounds as s, t, f, p, sh, ch and k.

Prior art artificial speech devices attempt to replace the larynx and vocal cords by introducing a standard oscillatory tone into the mouth itself, or blowing a similar tone on a path of air into the mouth, either of which can be referred to as illuminating the oral cavity, whereupon the tone is modulated by the mouth and detected by a listener as something resembling normal speech. However, when the tone introduced into the mouth for modulation is in the ultrasonic frequency range, some means must be provided to translate the ultrasonic signals into an audible frequency range. To produce speech from the translated signals representing speech, the signals must be synthesized into artificial speech. When synthesizing speech, the more the translated signals resemble human produced signals, the more likely the artificial speech will resemble natural speech. Thus, if the tone introduced into the mouth is a waveform resembling the waveforms produced by the vocal cords (glottal pulses rather than oscillatory waves as taught by the prior art), then the speech produced will more closely resemble human speech.

Figure 3:
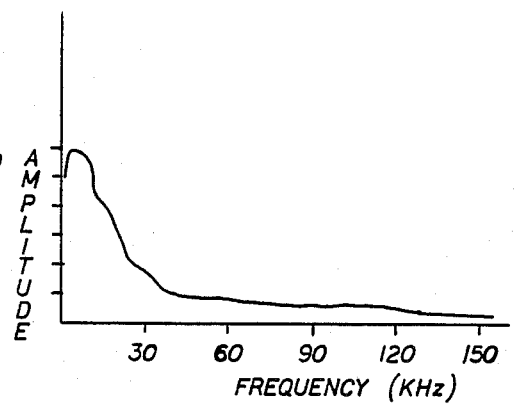
FIG. 3 is a graph illustrating the ultrasonic frequency spectrum of a glottal pulse shaped waveform in accordance with a preferred embodiment of the present invention.
Figure 2:
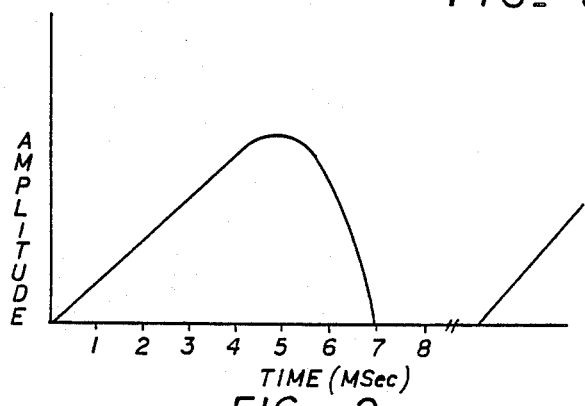
FIG. 2 is a graph illustrating a glottal pulse shaped waveform in accordance with a preferred embodiment of the present invention, and depicting the relationship between tone amplitude versus time.

FIG. 2 graphically illustrates a glottal pulse shaped waveform which can be used in accordance with the preferred embodiment of the present invention. The glottal pulse of FIG. 2 depicts the relationship between the amplitude of the glottal pulse over time. Although the glottal pulse waveform some what resembles a sine (oscillatory) waveform, significant differences exist between the two waveforms, namely the glottal pulse experiences a longer rise time and fast fall time. If an ultrasonic glottal pulse signal is analyzed by a frequency analysis system or spectrum, analyzer, a frequency spectrum, resembling the signal graphed in FIG. 3, can be produced. It should be noted that the amplitude of the signal of FIG. 3 is highest in the below 30 kilohertz range, where the fundamental frequency and the first couple of harmonics are located.

Figure 4A:
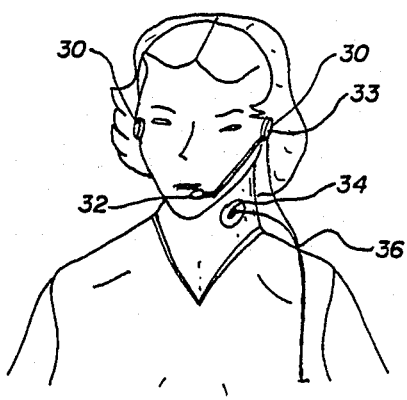
FIG. 4A is an illustration of an ultrasonic glottal pulse vibrator and ultrasonic receiver application of a preferred embodiment of the present invention.
Figure 4B:
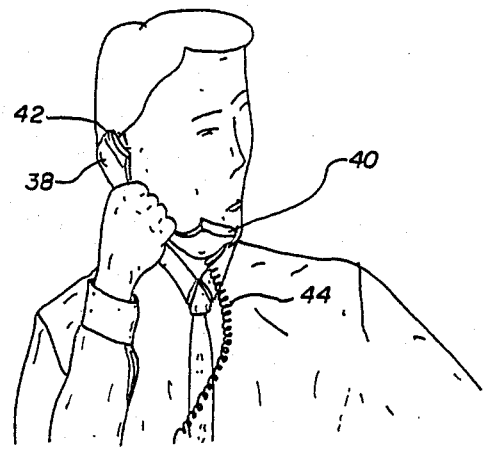
FIG. 4B is an illustration of an ultrasonic transducer and receiver as utilized in a telephonic application of a preferred embodiment of the present invention.

Two applications of a preferred embodiment of the present invention are illustrated in FIGS. 4A and 4B. FIG. 4A depicts a woman wearing a head set, having two speakers 30 and a receiver and/or transmitter 32 held before the woman's mouth by an arm 33. In place of the transmitter 32, a vibration device 34 may be placed on the woman's throat, in the approximate area of the larynx 16. The vibration device 34 causes the vocal tract to oscillate at an ultrasonic frequency, thereby causing ultrasonic signals vibration within the vocal track, which may be modulated by the mouth into words. Either way, ultrasonic signals are radiated from the mouth of the woman, whereupon they illuminate the oral cavity and are in return picked up by the ultrasonic microphone contained within arm 33. An ultrasonic microphone is used to filter out sounds within the audible range (below 13,500 Hz) so that only ultrasonic speech is transmitted to the translator and synthesizer along the wire 36. Speakers 30 may be used to provide a side-tone to the woman after translation and synthesization so she can monitor the quality and amplitude of her speech as spoken.

FIG. 4B depicts a similar application in which a telephone 38, having a transmitter and receiver in the mouth piece 40, and a speaker in the ear piece 42, transmits and receives signals over the cable 44 for either transmission or translation and synthesization. Cable 44 may also be used to recommunicate synthesized signals back up to the speakers 42, where the synthesized speech may be monitored as a side-tone in the ear of the speaker.

Figure 5:
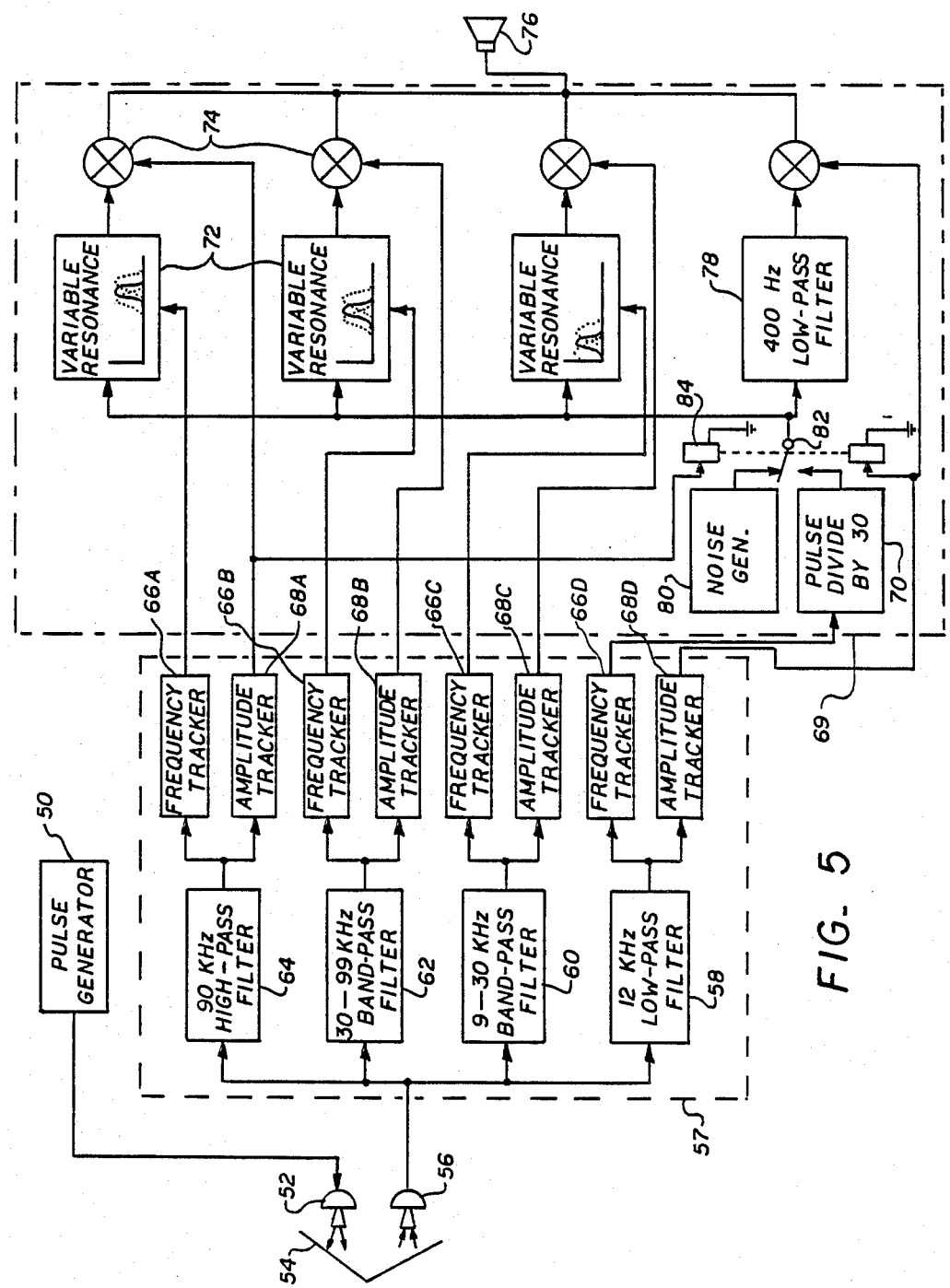
FIG. 5 is a diagram schematically illustrating the application of an ultrasonic vocoder in accordance with a preferred embodiment of the present invention.

Since the amplitude modulated signals detected by the microphone are not in the audible range when radiated from the mouth, the signals must be translated into corresponding signals in the audible frequency range, if they are to be used to produce speech. The same signals can also be used to operate certain machinery, and in such applications, there is no need to convert the signals into audible tones. Translation may be accomplished through the use of a modified vocoder, or similar device, which is capable of translating the ultrasonic speech into audible speech signals. In FIG. 5, a pulse generator 50 is used to produce a series of glottal pulses in the ultrasonic frequency range for communication to vibrator or transmitter 52. The ultrasonic glottal pulses are introduced into the vocal track and then reradiated by the mouth 54 as ultrasonic speech. The ultrasonic speech can then be picked up by receiver 56 and communicated to the translator 57.

Translator 57 has four filters which split the ultrasonic speech signals into four separate bands. The 12 Kilohertz low-pass filter 58 basically covers the fundamental frequency of both the average male and female speaker, while the 9 kilohertz to 30 kilohertz band-pass filter 60, the 30 kilohertz to 99 kilohertz band-pass filter 62, and the 90 kilohertz high-pass filter 64 covering the remainder of the frequency spectrum. The four bands as separated by the filters 58–64 are then transferred to separate frequency tracking circuits 66A–D and amplitude tracking circuits 68A–D, which track the ultrasonic speech formats. Frequency and amplitude tracking circuits 66 and 68 separate the frequency and amplitude components of the ultrasonic speech signals, track the ultrasonic speech formats, and output the signals to synthesizer 69.

The output of frequency tracking circuit 66D is input to a pulse divider 70, which divides the frequency component of the 12 kilohertz band by 30 and outputs a synchronization pulse for controlling the variable resonance circuits 72 and the 400 Hz low-pass filter 78. Variable resonance circuits 72 produce converted speech signals with corresponding frequencies in the audio spectrum of 300 hertz to 3500 hertz for transmission to the summing circuits 74. The output of noise generator 80 is switched by switch 82 with the output of pulse divider 70 to create the non-vocal hissing noises that are made by the teeth, lips and tongue, and which are required to make certain sounds. The control of switch 82 is maintained by solenoid 84, which operates under control of input signals from amplitude tracking circuit 68A, which indicates when speech signals are in the higher frequency range and noise generation is not required. Provisions may also be made to shift the audible voice tones into pitches that more closely resemble that of the speaker, for instance, male or female. Summing circuits 74 recombine all of the signals for transmission to speaker 76, where the artificial speech is audibly reproduced.

Figure 6:
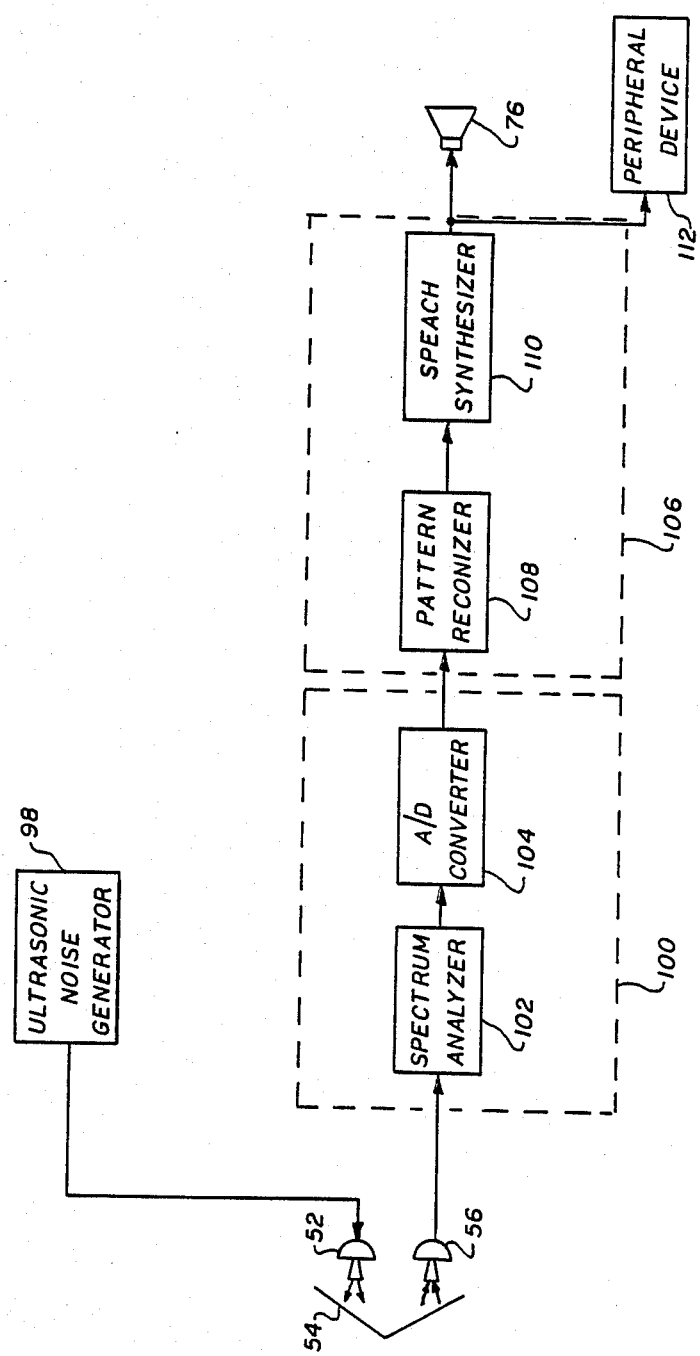
FIG. 6 is a diagram schematically illustrating an alternative embodiment of the present invention for converting ultrasonic words into audible speech.

FIG. 6 illustrates an alternative embodiment of the present invention in which ultrasonic noise generator 98 and ultrasonic transducer 52 drive a signal into mouth 54, where it is modulated into ultrasonic speech and is picked up by receiver 56 and communicated to a converter 100. The converter 100 is comprised of a spectrum analyzer 102 which segments the analog wave form communicated from receiver 56 into a plurality of discernable values and an analog-to-digital converter 104 which converts the segmented analog waveform into a digital representation, or in other words, a digitized spectral signature of the ultrasonic speech.

The digitized spectral signature of the ultrasonic speech is then communicated to speech generator 106, which translates the digitized spectral signature into audible speech. Speech generator 106 includes a pattern recognizer 108 which utilizes speech recognition techniques for generating a signal which can be synthesized by speech synthesizer 110 into electrical signals representing audible speech. The output of speech synthesizer 110 is then communicated to speaker 76, which produces audible artificial speech from the electrical signals.

It should also be noted that the primary function of either the preferred or alternative embodiment need not be speech production. As is demonstrated by FIG. 6, the input to speaker 76 may also be used to input signals to a peripheral device 112, such as a conveyor system or robot. Such a feature allows a worker in a noisy environment to operate a machine from a distance through ultrasonic voice communication.

Although the present invention has been described above in terms of a preferred embodiment, it is contemplated that numerous alterations and modifications of the invention will be apparent to those skilled in the art after having read the above disclosure. It is therefore intended that the following claims be interpreted as covering all such modifications and alterations as fall within the true spirit and scope of the invention.

I claim:

1. An artificial speech generation device, comprising:
   transmitting means for producing an ultrasonic signal and introducing said ultrasonic signal into the vocal track of a speaker for modulation of said ultrasonic signal by said speaker into ultrasonic words;
   detector means for receiving said ultrasonic words and generating an ultrasonic word signal corresponding to said ultrasonic words; and
   converter means for receiving said ultrasonic word signal and shifting said ultrasonic word signal into a corresponding artificial speech signal which can be utilized to create an audio signal corresponding to said speaker's ultrasonic words.

2. An artificial speech generation device as recited in claim 1, wherein said ultrasonic signal is a series of glottal shaped pulses.

3. An artificial speech generation device as recited in claim 1, wherein said ultrasonic signal is an oscillatory shaped wave form.

4. An artificial speech generation device as recited in claim 1, wherein said transmitting means is comprised of:
   signal generator means for producing and outputting said ultrasonic signal; and
   dispatching means for receiving said ultrasonic signal from said signal generator means and transmitting said ultrasonic signal into the vocal track of said speaker.

5. An artificial speech generation device as recited in claim 4, wherein said dispatching means is an ultrasonic transducer positioned so as to direct said ultrasonic signal into the vocal track of said speaker.

6. An artificial speech generation device as recited in claim 5, wherein said converter means is comprised of:

speech translation means responsive to said ultrasonic word signal and operative to convert said ultrasonic word signal to said artificial speech signal; and playback means for receiving said artificial speech signal and producing an audio signal representation thereof for playback to said speaker.

7. An artificial speech generation device as recited in claim 6, wherein said speech translation means includes:

translator means for receiving said ultrasonic word signal and operative to separate said ultrasonic word signal into a plurality of frequency bands, to track the frequency and amplitude component of each said frequency band, and to develop separate corresponding amplitude and frequency component signals for output therefrom; and synthesizer means for receiving said amplitude and frequency component signals input from said translator means and operative to produce said artificial speech signal.

8. An artificial speech generation device as recited in claim 7, wherein said synthesizer means includes:

a plurality of variable resonance circuits for receiving said amplitude and frequency component signals and operative to produce corresponding amplitude and frequency signals in the audio spectrum;

noise generating means for producing an electrical noise signal corresponding to the non-vocal noises required for the production of comprehensible speech; and summation means for receiving said amplitude and frequency signals in the audio spectrum and said electrical noise signal and operative to combine said amplitude and frequency signals in the audio spectrum with said electrical noise signals so as to produce said artificial speech signal.

9. An artificial speech generation device as recited in claim 8, wherein said plurality of variable resonance circuits are operated at about one-thirtieth of the frequency of said ultrasonic signal introduced by said transmitting means.

10. An artificial speech generation device as recited in claim 6, wherein said speech translation means is a vocoder circuit.

11. An artificial speech generation device as recited in claim 4, wherein said dispatching means is an ultrasonic vibrator positioned so as to introduce said ultrasonic signal into the vocal track of said speaker.

12. An artificial speech generation device as recited in claim 11, wherein said converter means is comprised of:

speech translation means responsive to said ultrasonic word signal and operative to convert said ultrasonic word signal to said artificial speech signal; and playback means for receiving said artificial speech signal and producing an audio signal representation thereof for playback to said speaker.

13. An artificial speech generation device as recited in claim 12, wherein said speech translation means includes:

translator means for receiving said ultrasonic word signal and operative to separate said ultrasonic word signal into a plurality of frequency bands, to track the frequency and amplitude component of each said frequency band, and to develop separate corresponding amplitude and frequency component signals for output therefrom; and synthesizer means for receiving said amplitude and frequency component signals input from said translator means and operative to produce said artificial speech signal.

14. An artificial speech generation device as recited in claim 13, wherein said synthesizer means includes:

a plurality of variable resonance circuits for receiving said amplitude and frequency component signals and operative to produce corresponding amplitude and frequency signals in the audio spectrum;

noise generating means for producing an electrical noise signal corresponding to the non-vocal noises required for the production of comprehensible speech; and summation means for receiving said amplitude and frequency signals in the audio spectrum and said electrical noise signal and operative to combine said amplitude and frequency signals in the audio spectrum with said electrical noise signals so as to produce said artificial speech signal.

15. An artificial speech generation device as recited in claim 14, wherein said plurality of variable resonance circuits are operated at about one-thirtieth of the frequency of said ultrasonic signal introduced by said transmitting means.

16. An artificial speech generation device as recited in claim 12, wherein said speech translation means is a vocoder circuit.

17. An artificial speech generation device as recited in claim 1, wherein said converter means is comprised of:

speech translation means responsive to said ultrasonic word signal and operative to convert said ultrasonic word signal to said artificial speech signal; and playback means for receiving said artificial speech signal and producing an audio signal representation thereof for playback to said speaker.

18. An artificial speech generation device as recited in claim 17, wherein said speech translation means includes:

translator means for receiving said ultrasonic word signal and operative to separate said ultrasonic word signal into a plurality of frequency bands, to track the frequency and amplitude component of each said frequency band, and to develop separate corresponding amplitude and frequency component signals for output therefrom; and synthesizer means for receiving said amplitude and frequency component signals input from said translator means and operative to produce said artificial speech signal.

19. An artificial speech generation device as recited in claim 18, wherein said synthesizer means includes:

a plurality of variable resonance circuits for receiving said amplitude and frequency component signals and operative to produce corresponding amplitude and frequency signals in the audio spectrum;

noise generating means for producing an electrical noise signal corresponding to the non-vocal noises required for the production of comprehensible speech; and summation means for receiving said amplitude and frequency signals in the audio spectrum and said electrical noise signal and operative to combine said amplitude and frequency signals in the audio spectrum with said electrical noise signals so as to produce said artificial speech signal.

20. An artificial speech generation device as recited in claim 19, wherein said plurality of variable resonance circuits are operated at about one-thirtieth of the frequency of said ultrasonic signal introduced by said transmitting means.

21. An artificial speech generation device as recited in claim 17, wherein said speech translation means is a vocoder circuit.

22. An artificial speech generation device, comprising:
   transmitting means for producing an ultrasonic signal and introducing said ultrasonic signal into the vocal track of a speaker for modulation of said ultrasonic signal by said speaker into ultrasonic words;
   detector means for receiving said ultrasonic words and generating an ultrasonic word signal corresponding to said ultrasonic words;
   converter means for receiving said ultrasonic word signal and converting said ultrasonic word signal into a series of analog spectral signatures representing said ultrasonic words and developing a digitized spectral signature signal therefrom; and
   generating means for receiving said digitized spectral signature signal and operative to generate an audible speech communication signal from said digitized spectral signature signal.

23. An artificial speech generation device as recited in claim 22, wherein said converter means includes:
   spectrum analyzer means for receiving said ultrasonic word signal and developing said analog spectral signature therefrom; and
   digitizing means for receiving said analog spectral signature signal and operative to develop said digitized spectral signature signal.

24. An artificial speech generation device as recited in claim 23, wherein said generating means includes:
   means for receiving said digitized spectral signature signal and operative to recognize and to separate each of a plurality of speech components contained within said digitized spectral signature signal, and to develop a corresponding speech component signal containing each of said plurality of speech components; and
   synthesizing means for receiving said speech component signal and operative to synthesize each speech component of said plurality of speech components contained within said speech component signal into said audible speech communication signal.

25. An artificial speech generation device as recited in claim 24, wherein said generating means further includes a broadcasting means for receiving said audible speech communication signal and producing audible speech therefrom.

26. A method for generating non-audible speech communication signals, comprising the steps of:
   transmitting an ultrasonic signal into the vocal track of a speaker;
   modulating said ultrasonic signal within the vocal track of said speaker into ultrasonic words;
   communicating said ultrasonic words out of the vocal track of said speaker;
   detecting said ultrasonic words; and
   converting said ultrasonic words into non-audible speech communication signals which may be utilized to silently communicate operation commands to a plurality of devices responsive to said non-audible speech communication signals.

* * * * *